United States Patent [19]

Begley

[11] Patent Number: 5,362,880
[45] Date of Patent: Nov. 8, 1994

[54] METHOD OF PREPARING A MAGENTA DEVELOPMENT INHIBITOR RELEASING COUPLER

[75] Inventor: William J. Begley, Webster, N.Y.

[73] Assignee: Eastman Kodak Company, Rochester, N.Y.

[21] Appl. No.: 906,633

[22] Filed: Jun. 30, 1992

[51] Int. Cl.$^5$ .................. C07D 403/14; C07D 413/14; C07D 417/14; G03C 7/305
[52] U.S. Cl. .................................... 548/251; 548/142; 548/185; 548/229; 548/257; 430/544
[58] Field of Search ................................ 548/251, 257

[56] References Cited

U.S. PATENT DOCUMENTS

| | | | |
|---|---|---|---|
| 4,248,962 | 2/1981 | Lau | 430/382 |
| 4,409,323 | 10/1983 | Sato et al. | 430/544 |
| 4,861,701 | 8/1989 | Burns et al. | 430/543 |

FOREIGN PATENT DOCUMENTS 0540118  5/1993  European Pat. Off. .

*Primary Examiner*—David B. Springer
*Attorney, Agent, or Firm*—Andrew Alexander

[57] ABSTRACT

Disclosed is a method of preparing a photographic coupler comprised of 1-aryl-3-substituted-4-heterocyclic-5-pyrazolone development inhibitor releasing coupler for use in a photographic element, said coupler capable of reacting with oxidized color developer to release a heterocyclic coupling-off group containing an inhibitor.

4 Claims, No Drawings

METHOD OF PREPARING A MAGENTA DEVELOPMENT INHIBITOR RELEASING COUPLER

This invention relates to a photographic compound that releases a development inhibitor group upon oxidative coupling during photographic processing to enable increased activity, interlayer inter image and image acutance and to photographic materials and processes using such a compound. Wherein activity means the amount of compound needed to have an effect on the causer gamma described in the application. Various ways are recognized in the photographic art for releasing a development inhibitor group from a compound, such as a coupler, in a photographic material and process. For example, U.S. Pat. No. 4,248,962 describes compounds that release a photographically useful group, such as a development inhibitor group, by means of an intramolecular nucleophilic displacement reaction in photographic materials. Other examples of compounds, particularly couplers, that are capable of release of development inhibitor groups are described in U.S. Pat. Nos. 4,409,323 and 4,861,701 and Japanese Patent Application 56-73800, filed May 15, 1981. These compounds, particularly couplers, are capable of releasing a development inhibitor group in a photographic material upon processing with a degree of control over timing and rate of release as well as the rate and distance of diffusion of the development inhibitor group in the photographic material.

A need has existed for a method of preparing a compound, preferably a coupler, that not only provides the described release of a development inhibitor group, but also provides increased acutance for the image provided upon processing the photographic material containing the compound. Moreover, such a need has existed with the added parameter that such a compound must not require significantly modifying the development inhibitor groups or the carrier compound, such as the couplers, in such a way that would adversely affect the ultimate end use for which each is intended.

The present invention solves this problem by providing a method for preparing a 1-aryl-3-substituted-4-heterocyclic-5-pyrazole development inhibitor releasing coupler (A) for use in a photographic element comprising a support bearing at least one photographic silver halide emulsion layer and at least one development inhibitor releasing compound (A) represented by the formula CAR-BTAZ-Q where CAR is a carrier moiety, preferably a coupler moiety, capable of releasing BTAZ-Q during photographic processing upon reaction with oxidized developing agent, BTAZ is a benzotriazole nucleus; and BTAZ-Q is represented by the formula:

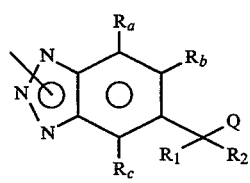

wherein:
$R_a$, $R_b$, $R_c$, $R_1$ and $R_2$ individually are hydrogen, substituted or unsubstituted alkyl or aryl containing 1–12 carbon atoms, or halogen, nitro, ester, amide, or $R_1$ and $R_2$ together can complete a substituted or unsubstituted 5, 6 or 7 membered ring system, particularly a spiro system;

Q is a development inhibitor group.

BTAZ-Q, as described enables formation of an image upon processing the photographic element that has increased acutance, interlayer interimage and activity. It is thought that the presence of the BTAZ and Q groups in the described sequence may aid formation of an image having the desired properties. Similar BTAZ and Q moieties alone, which do not contain the combination of groups as described, also do not provide the required increased acutance, interlayer interimage and activity as shown by the comparative data in the examples. Examples of such BTAZ-Q groups are represented by the following:

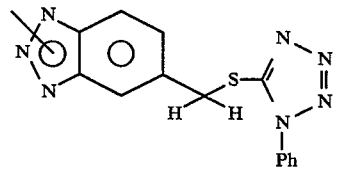

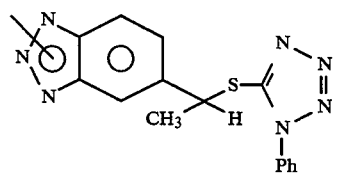

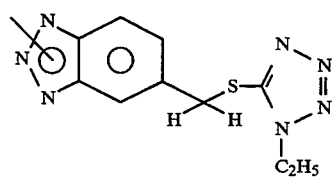

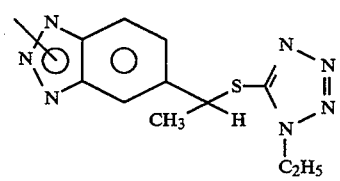

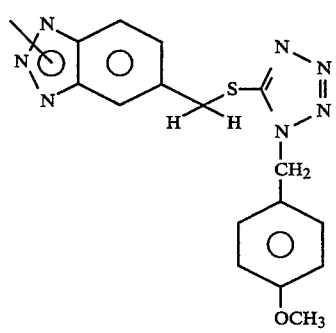

-continued

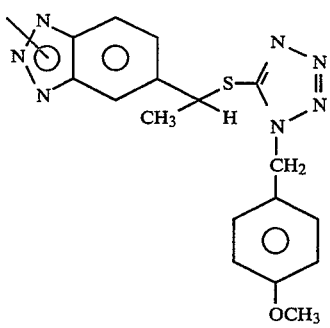

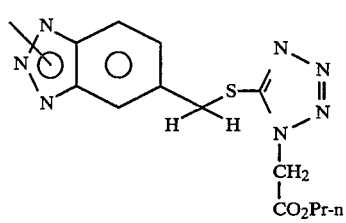

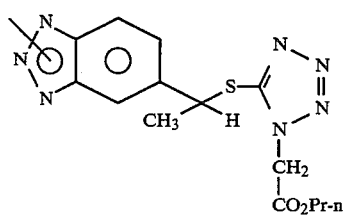

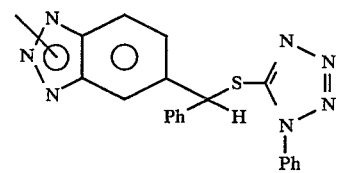

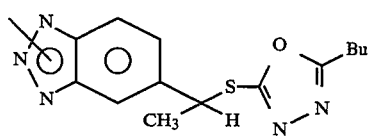

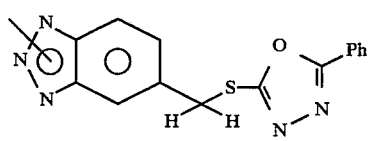

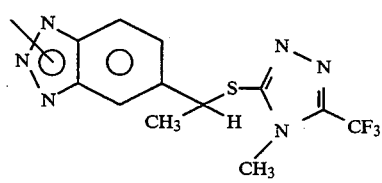

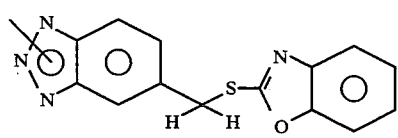

-continued

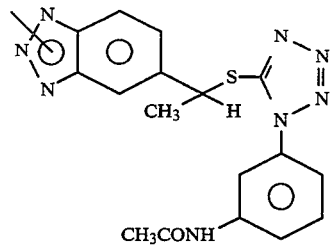

A preferred compound (A) is a dye-forming coupler of the form COUP-BTAZ-Q in which COUP is a coupler moiety, such as a cyan, magenta or yellow dye-forming coupler moiety, and BTAZ-Q is a coupling-off group.

A process of forming an image having the described increased acutance, interlayer interimage and activity comprises developing an exposed photographic silver halide element by means of a color developing agent in the presence of described compound (A), particularly a coupler as described.

Illustrative preferred BTAZ-Q groups are represented by the formula:

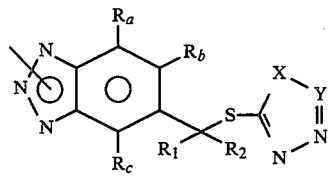

wherein:
$R_a$, $R_b$, $R_c$ $R_1$ and $R_2$ individually are hydrogen, substituted or unsubstituted alkyl or aryl containing 1–12 carbon atoms, or halogen, nitro, ester, amide or $R_1$ and $R_2$ can complete a substituted or unsubstituted 5, 6, or 7-membered ring system, particularly a spiro system;

X is a divalent group such as oxygen, sulfur, or $NR_3$ where $R_3$ can be substituted or unsubstituted alkyl or aryl;

Y can be nitrogen or $CR_4$ where C is carbon and $R_4$ can be substituted or unsubstituted alkyl or aryl.

The reaction of compound (A), preferably a development inhibitor releasing (DIR) coupler, with oxidized color developing agent cleaves the bond between the coupling-off group (BTAZ-Q) and the carrier portion of the compound (A), preferably the coupler moiety (COUP). Tailoring of the structure of the part BTAZ-Q allows control of the desired characteristics of the resulting image in the photographic material.

Particularly useful compounds as described are couplers represented by the formulas:

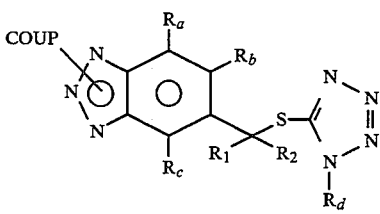

-continued

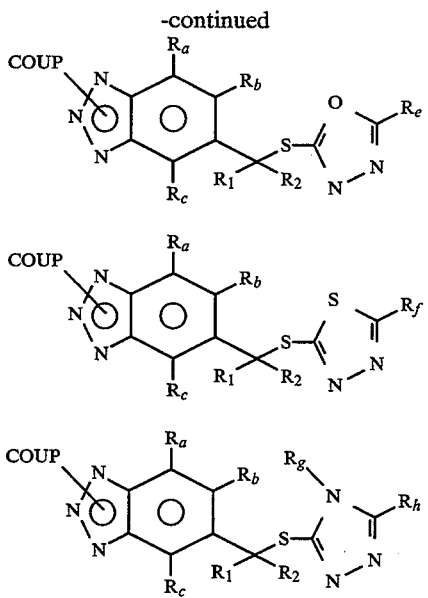

wherein
COUP is a coupler moiety, such as a cyan, magenta or yellow dye forming coupler moiety;

$R_{a-h}$, $R_1$ and $R_2$ individually are hydrogen, substituted or unsubstituted alkyl or aryl containing 1–12 carbon atoms, or halogen, nitro, ester, amide, or $R_1$ and $R_2$ together can complete a substituted or unsubstituted 5, 6 or 7 membered ring system, particularly a spiro system;

$R_g$ and $R_h$ together may complete a ring system

The coupler moiety (COUP) can be any moiety that will react with oxidized color developing agent to cleave the bond between the COUP and the BTAZ-Q. The coupler moiety includes coupler moieties that have been used in conventional color-forming couplers in the photographic art to yield colorless products upon reaction with oxidized color developing agents or yield color products on reaction with oxidized color developing agents.

The coupler moiety can be ballasted or unballasted. It can be monomeric, or it can be a dimeric, oligomeric or polymeric coupler, in which case it will contain more than one BTAZ-Q group.

The coupling-off group (BTAZ-Q) is joined to the coupler moiety at a coupling position of the coupler moiety. The coupling-off group is released from the coupling position by oxidative coupling reactions known in the photographic art.

The group Q can be any releasable development inhibitor group known to be useful in the photographic art. The group Q can be present as a preformed species or it can be present as a blocked form or as a precursor. Particularly, the Q group can be a preformed development inhibiting group or the development inhibitor can be blocked.

Preferred compound (A) is a photographic coupler containing a ballasted coupler moiety and a Q group that contains a sulfur atom bonded to the α-carbon atom on the arylene ring of the BTAZ group in BTAZ-Q.

The method of preparing the photographic coupler comprised of 1-aryl-3-substituted-4-heterocyclic-5-pyrazolone development inhibitor releasing coupler for use in a photographic element includes, (a) reacting an α-haloacylanilide with a heterocyclic moiety in the presence of a base to produce a first product;
(b) thereafter reacting the first product with a hydrazine to form a pyrazolone compound;
(c) adding a photographic ballast to the pyrazolone compound; and
(d) reacting the ballasted pyrazolone compound with an inhibitor after reduction and halogenation of the pyrazolone compound to form the 1-aryl-3-substituted-4-heterocyclic-5-pyrazolone development inhibitor releasing coupler.

The hydrazine has the structure:

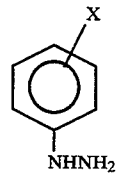

wherein X is selected from nitro, methoxy, chloro, bromo, substituted amino, esters, carbonamido, carboxyl, hydroxyl, sulfo, sulfonamido, carbamoyl, sulfamoyl, substituted or unsubstituted alkyl containing 1 to 40 carbon atoms, and substituted or unsubstituted aryl containing 6 to 40 carbon atoms.

The heterocyclic moiety can have a photographic development inhibitor group attached thereto prior to reacting with the α-haloacylanilide.

Further, the heterocyclic moiety can have an alcohol group attached thereto. After formation of the pyrazolone and the attachment of the ballast the pyrazolone compound may be halogenated and the inhibitor group attached.

A listing of patents follows that describes representative COUP groups useful in the invention. The coupling-off group in each case can be BTAZ-Q as described.

COUP's I

A. Couplers which form cyan dyes upon reaction with oxidized color developing agents are described in such representative patents and publications as: U.S. Pat. Nos. 2,772,162; 2,895,826; 3,002,836; 3,034,892; 2,474,293; 2,423,730; 2,367,531; 3,041,236; 4,333,999 and "Farbkuppler-eine Literaturubersicht," published in Agfa Mitteilungen, Band III, pp. 156–175(1961).

Preferably such couplers are phenols and naphthols which form cyan dyes on reaction with oxidized color developing agent.

B. Couplers which form magenta dyes upon reaction with oxidized color developing agent are described in such representative patents and publications as : U.S. Pat. Nos. 2,600,788; 2,369,489; 2,343,703; 2,311,082; 3,152,896; 3,519,429; 3,062,653; 2,908,573 and "Farbkuppler-eine Literaturubersicht," published in Agfa Mitteilungen, Band III, pp. 126–156 (1961).

Preferably, such couplers are pyrazolones and pyrazolotriazoles which form magenta dyes upon reaction with oxidized color developing agents and have the BTAZ-Q attached to the coupling position.

C. Couplers which form yellow dyes upon reaction with oxidized and color developing agent are described in such representative patents and publications as: U.S. Pat. Nos. 2,875,057; 2,407,210; 3,265,506; 2,298,443; 3,048,194; 3,447,928 and "Farbkuppler-eine Literaturubersicht," published in Agfa Mitteilungen, Band III, pp. 112–126 (1961).

Preferably such yellow-dye forming couplers are acylacetamides, such as benzoylacetanilides and pivaloylacetanilides, and have the BTAZ-Q group attached to the coupling position, that is the active methylene carbon atom.

D. Couplers which form colorless products upon reaction with oxidized color developing agent are described in such representative patents as: U.K. Patent No. 861,138; U.S. Pat. Nos. 3,632,345; 3,928,041; 3,958,993 and 3,961,959.

Preferably such couplers are cyclic carbonyl containing compounds which form colorless products on reaction with oxidized color developing agent.

Illustrative releasable development inhibitor groups (Q) are described in such representative patents as U.S. Pat. Nos. 3,227,554; 3,384,657; 3,615,506; 3,617,291; 3,733,201 and U.K. Pat. No. 1,450,479. Preferred development inhibitors are iodide and heterocyclic compounds such as mercaptotetrazoles, selenotetrazoles, mercaptobenzothiazoles, selenobenzothiazoles, mercaptobenzoxazoles, selenobenzoxazoles, mercaptobenzimidazoles, selenobenzimidazoles, oxadiazoles, benzotriazoles and benzodiazoles. Structures of preferred development inhibitor moieties are:

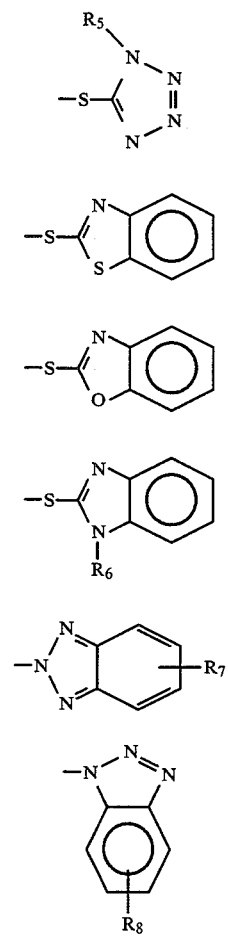

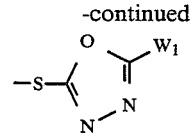

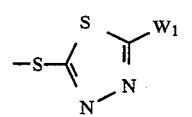

where W1 is unsubstituted or substituted alkyl or aryl, such as butyl, 1-ethylpentyl, and 2-ethoxyethyl, or alkylthio, such as butylthio and octylthio; $R_5$ and $R_6$ are individually hydrogen, alkyl of 1 to 8 carbon atoms such as methyl, ethyl, or butyl, phenyl or substituted phenyl; and $R_7$ and $R_8$ are individually hydrogen or one or more halogen such as chloro, fluoro or bromo; alkyl of 1 to 4 carbon atoms, carboxyl, esters such as —COOCH$_3$, or other substituents such as —NHCOOCH$_3$, —SO$_2$OCH$_3$, —OCH$_2$CH$_2$SO$_2$CH$_3$, —OC(O)OCH$_2$CH$_3$, —NHC(O)C(O)OCH$_3$ or nitro groups.

The photographic couplers of this invention can be incorporated in photographic elements and/or in photographic processing solutions, such as developer solutions, so that upon development of an exposed photographic element they will be in reactive association with oxidized color developing agent. Coupler compounds incorporated in photographic processing solutions should be of such molecular size and configuration that they will diffuse through photographic layers with the processing solution. When incorporated in a photographic element, as a general rule, the coupler compounds should be nondiffusible, that is they should be of such molecular size and configuration that they will not significantly diffuse or wander from the layer in which they are coated.

Photographic elements of this invention can be processed by conventional techniques in which color forming couplers and color developing agents are incorporated in separate processing solutions or compositions or in the element.

Photographic elements in which the compounds of this invention are incorporated can be a simple element comprising a support and a single silver halide emulsion layer or they can be multilayer, multicolor elements. The compounds of this invention can be incorporated in at least one of the silver halide emulsion layers and/or in at least one other layer, such as an adjacent layer, where they will come into reactive association with oxidized color developing agent which has developed silver halide in the emulsion layer. The silver halide emulsion layer can contain or have associated with it, other photographic coupler compounds, such as dye-forming couplers, colored masking couplers, and/or competing couplers. These other photographic couplers can form dyes of the same or different color and hue as the photographic couplers of this invention. Additionally, the silver halide emulsion layers and other layers of the photographic element can contain addenda conventionally contained in such layers.

A typical multilayer, multicolor photographic element can comprise a support having thereon a red-sensitive silver halide emulsion unit having associated therewith a cyan dye image-providing material, a green-sensitive silver halide emulsion unit having associated therewith a magenta dye image-providing material and a blue-sensitive silver halide emulsion unit having associated therewith a yellow dye image-providing material, at least one of the silver halide emulsion units having associated therewith a photographic coupler of the invention. Each silver halide emulsion unit can be composed of one or more layers and the various units and layers can be arranged in different locations with respect to one another.

The couplers of this invention can be incorporated in or associated with one or more layers or units of the photographic element. For example, a layer or unit affected by BTAZ-Q can be controlled by incorporating in appropriate locations in the element a scavenger layer which will confine the action of BTAZ-Q to the desired layer or unit. At least one of the layers of the photographic element can be, for example, a mordant layer or a barrier layer.

The light sensitive silver halide emulsions can include coarse, regular or fine grain silver halide crystals or mixtures thereof and can be comprised of such silver halides as silver chloride, silver bromide, silver bromoiodide, silver chlorobromide, silver chloroiodide, silver chlorobromoiodide and mixtures thereof. The emulsions can be negative-working or direct-positive emulsions. They can form latent images predominantly on the surface of the silver halide grains or predominantly on the interior of the silver halide grains. They can be chemically and spectrally sensitized. The emulsions typically will be gelatin emulsions although other hydrophilic colloids are useful. Tabular grain light sensitive silver halides are particularly useful such as described in *Research Disclosure*, Jan. 1983, Item No. 22534 and U.S. Pat. No. 4,434,226.

The support can be any support used with photographic elements. Typical supports include cellulose nitrate film, cellulose acetate film, polyvinylacetal film, polyethylene terephthalate film, polycarbonate film and related films or resinous materials as well as glass, paper, metal and the like. Typically, a flexible support is employed, such as a polymeric film or paper support. Paper supports can be acetylated or coated with baryta and/or an a-olefin polymer, particularly a polymer of an a-olefin containing 2 to 10 carbon atoms such as polyethylene, polypropylene, ethylene-butene copolymers and the like.

The compound (A), particularly photographic couplers, as described, can be used in photographic elements in the same way as photographic couplers that release development inhibitor groups have previously been used in the photographic art. The compound (A) as described can be contained in, or in reactive association with, one or more of the silver halide emulsion units in a color photographic element. If the silver halide emulsion unit is composed of more than one layer, one or more of such layers can contain one or more of the compound (A), particularly the coupler (COUP-BTAZ-Q) as described.

In the following discussion of suitable materials for use in the emulsions and elements of this invention, reference will be made to *Research Disclosure*, Dec. 1978, Item 17643, published by Industrial Opportunities Ltd., Homewell Eavant, Hampshire, P09 1EF, U.K., the disclosures of which are incorporated herein by reference. This publication will be identified hereafter by the term "Research Disclosure".

The photographic elements can be coated on a variety of supports as described in Research Disclosure Section XVII and the references described therein.

Photographic elements can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the element with a color developing agent to reduce developable silver halide and oxidize the color developing agent. Oxidized color developing agent in turn reacts with the coupler to yield a dye.

Preferred color developing agents useful in the invention are p-phenylene diamines. Especially preferred are 4-amino-N,N-diethylaniline hydrochloride; 4-amino-3-methyl-N,N-diethylaniline hydrochloride; 4-amino-3-methyl-N-ethyl-N-$\beta$(methanesulfonamido)ethylaniline sulfate hydrate; 4-amino-3-methyl-N-ethyl-N-$\beta$-hydroxyethylaniline sulfate; 4-amino-3-$\beta$-(methanesulfonamido)-ethyl-N,N-diethylaniline hydrochloride; and 4-amino-N-ethyl-N-(2-methoxyethyl)-m-toluidine di-p-toluenesulfonic acid.

With negative working silver halide the processing step described above gives a negative image. To obtain a positive (or reversal) image, this step can be preceded by development with a non-chromogenic developing agent to develop exposed silver halide, but not form a dye, and then uniformly fogging the element to render unexposed silver halide developable. Alternatively, a direct positive emulsion can be employed to obtain a positive image.

The compounds as described can be prepared by reactions and methods described in the application. Typically, the couplers are prepared by first attaching a BTAZ-C(=O)R group to the coupling position without the Q group present. Then the product is reduced to the alcohol and converted to its halide. The halide is reacted with an appropriate derivative of the Q group to form the desired coupler. Alternatively, the Q group may be attached first to the BTAZ group and then the BTAZ-Q group is attached to the coupler moiety at the coupling position. The following synthesis illustrates the methods of preparation:

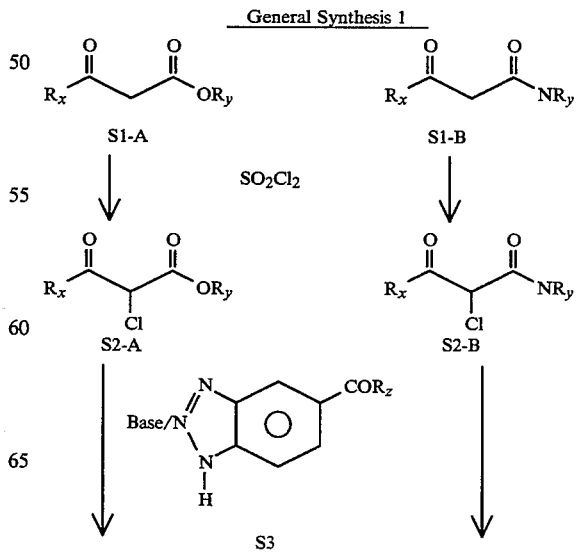

-continued
General Synthesis 1
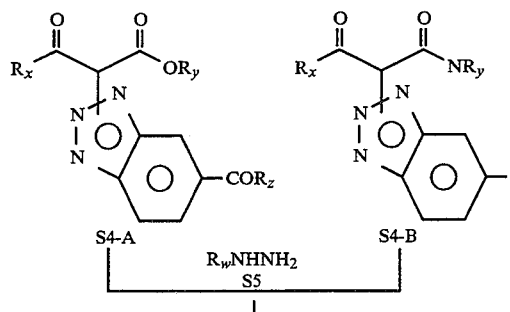
S4-A     S4-B
$R_w NHNH_2$
S5
General Synthesis 2
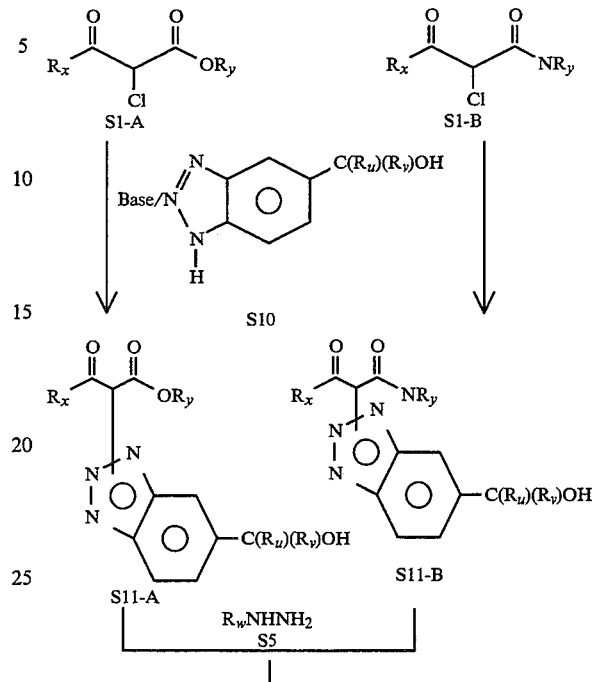
S1-A     S1-B
Base / S10
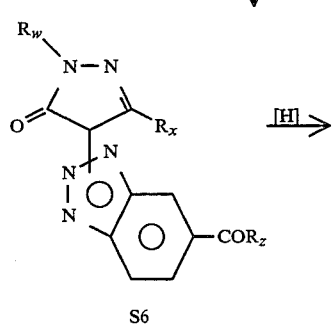
S6
[H] →
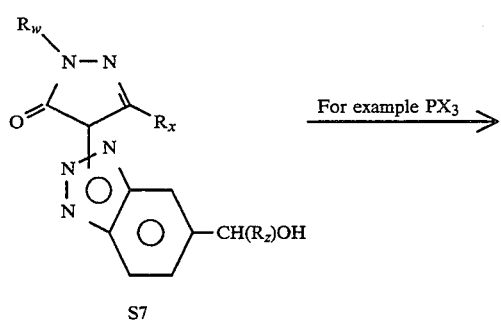
S11-A     S11-B
$R_w NHNH_2$
S5
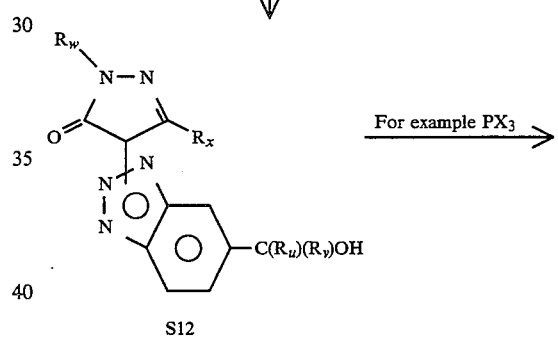
S7
For example $PX_3$ →
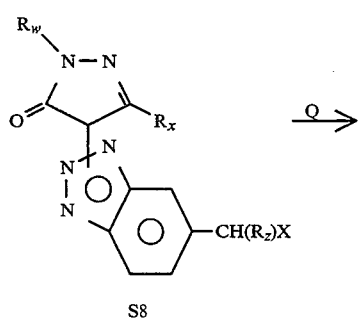
S12
For example $PX_3$ →
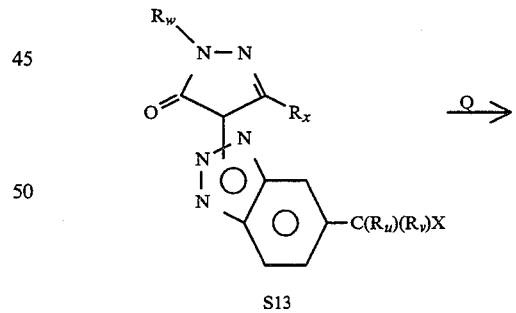
S8
Q →
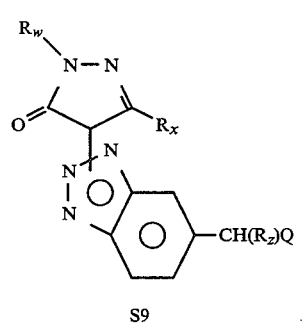
S9
S13
Q →
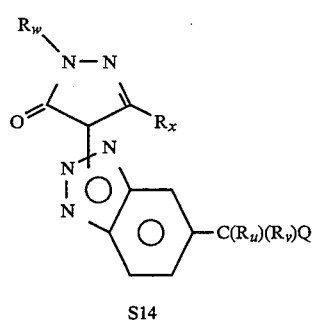
S14

In the above compounds $R_u$, $R_v$, $R_x$, $R_y$ and $R_z$ are hydrogen, substituted or unsubstituted alkyl or aryl. $R_w$ is substituted or unsubstituted alkyl or aryl. A ballast group, as known in the art, is located on $R_w$ or $R_x$. X is a halogen atom and Q is an inhibitor as described in the application.

In the described process compounds S1-A or S1-B are reacted with surphuryl chloride to give S2-A or S2-B either of which can be reacted with the BTAZ derivative S3 to give S4-A or S4-B. Reaction of S4-A or S4-B with the hydrazine S5 gives the 5-pyrazolone S6. Reduction of S6 to S7 followed by formation of its halide S8 and reaction of S8 with the inhibitor Q gives the desired coupler. Alternatively, S1-A or S1-B can be reacted with the reduced BTAZ derivative S10 to give S11-A or S11-B. S11-A or S11-B are then converted to the 5-pyrazolone S12 which is converted to its halide S13 and finally to the desired coupler S14.

The following examples further illustrate preparation of compounds of the invention Synthesis Example A

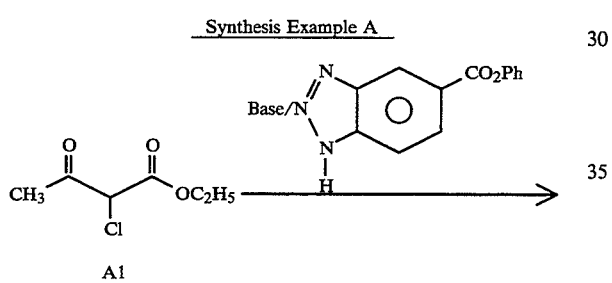

A1

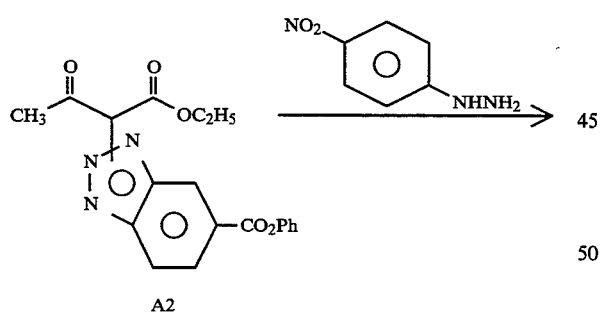

A2

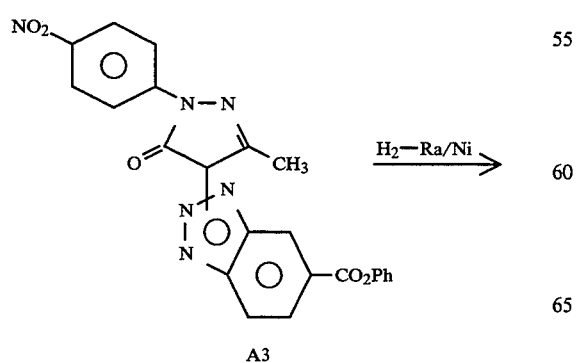

A3

Synthesis Example A

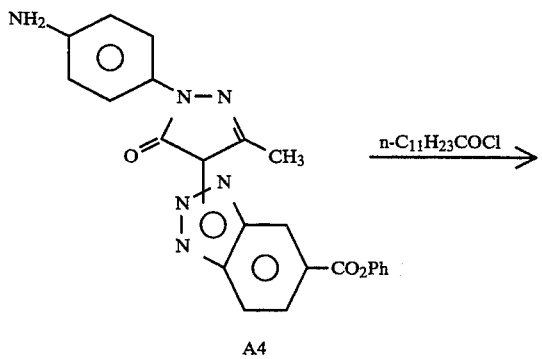

A4

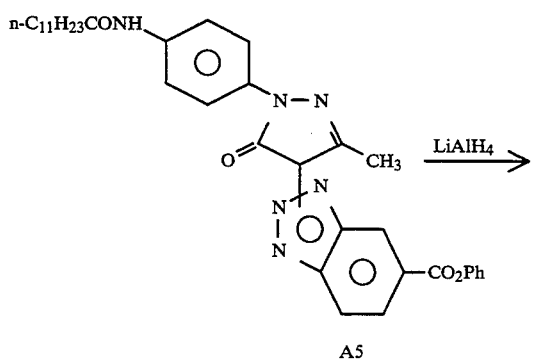

A5

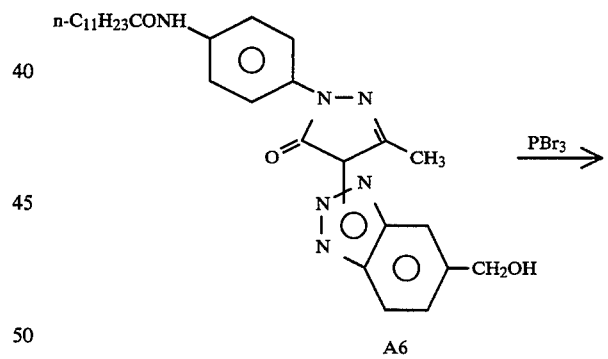

A6

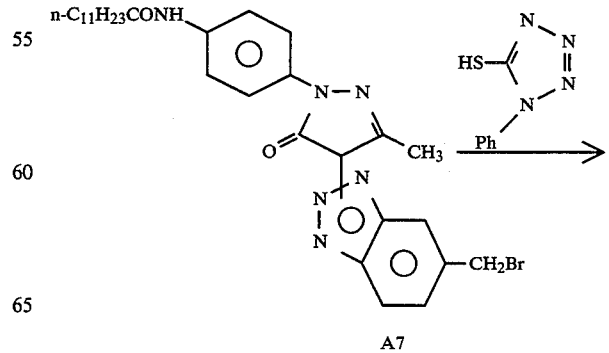

A7

-continued
Synthesis Example A

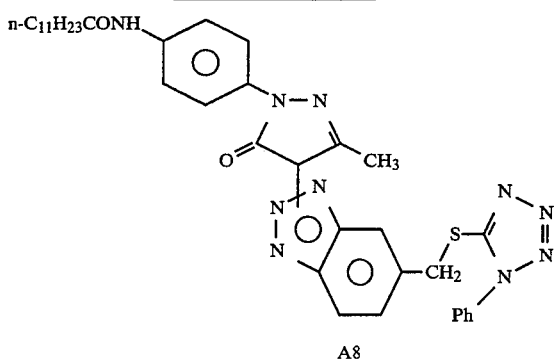

A8

Compound A2

Ethyl 2-chloroacetoacetate (20.0 g, 121.51 mMole), phenyl benzotriazole-5-carboxylate (26.43 g, 110.47 mMole) and triethylamine (16.9 mL, 121.51 mMole) were dissolved in dimethylformamide (200 mL) and stirred under a nitrogen atmosphere at room temperature for 12 hrs. At the end of this period the reaction mixture was diluted with ethyl acetate, washed with 2N-HCl (x2), dried (MgSO$_4$), filtered and concentrated to an oil. The residual oil was dissolved in a solvent mixture of ethyl acetate/heptane/dichloromethane/acetic acid in the ratio of 15:85:20:0.5 respectively, filtered and pressure chromatographed over silica gel eluting with the same solvent mixture. The major band was collected to give product A2. Yield: 36.0 g, 81%.

Compound A3

Compound A2 (16.0 g, 66.88 mMole), was dissolved in acetic acid (250 mL) and p-nitrophenylhydrazine hydrochloride (13.95 g, 73.57 mMole) added followed by anhydrous sodium acetate (6.04 g, 73.57 mMole). The resulting solution was heated gently on a steam bath to 90° C. for 1 hr, with stirring. After this period the reaction is filtered and the residual solid filtered off, washed with a little acetic acid and discarded. The mother liquor from the reaction and the washings were combined, poured into ice cold 2N—HCl and the yellow solid filtered off, washed well with water and air-dried. The resulting solid was dissolved in 8%-acetic acid in dichloromethane and pressure chromatographed over silica gel using the same solvent mixture to elute the impurities and changed to a mixture of dichloromethane/ethyl acetate/acetic acid in the ratio of 154:30:16 to collect the product, A3. Yield: 19.0 g, 62%.

Compound A4

Compound A3 (10.0 g, 21.9 mMole), was dissolved in tetrahydrofuran (30 mL) and methanol (150 mL). To this solution was added Raney-Nickel which had been prewashed with water and methanol and the mixture hydrogenated at 50 psi for approximately 2 hrs. At the end of this period the catalyst was filtered off, washed well with tetrahydrofuran and the solution and washings concentrated to a foam, compound A4. This foam was used directly in the next step without further purification.

Compound A5

Compound A4, (21.9 mMole), was dissolved in tetrahydrofuran (100 mL) to which was added N,N-dimethylaniline (5.55 mL, 43.82 mMole) and lauroyl chloride (5.0 mL, 21.9 mMole) in tetrahydrofuran (100 mL) added dropwise over a 15 minute period. After the addition of the acid chloride the reaction was stirred for a further 15 minutes at room temperature, and concentrated under reduced pressure. The residual oil was dissolved in ethyl acetate, washed with 2N-HCl (x3), dried (MgSO$_4$), filtered and concentrated. The residual oil crystallised from methanol as a white solid in two crops, one yielding 5.3 g, the second 4.2 g of compound A5. Total yield: 9.5 g, 71% from compound A3.

Compound A6

Compound A5, (7.0 g, 11.5 mMole) was dissolved in tetrahydrofuran (70 mL), the solution cooled to 0° C. and lithium aluminium hydride (0.44 g, 11.5 mMole) gradually added with efficient stirring. To get complete reaction a further batch of the reducing agent (0.44 g), had to be added. After stirring the reaction mixture at room temperature for about 1 hr., the reaction was carefully quenched with ethyl acetate then 2N—HCl. The resulting mixture was extracted with ethyl acetate (x3), dried (MgSO$_4$), filtered and concentrated under reduced pressure. On cooling and standing the residual oil crystallised from methanol to give compound A6. Yield: 4.0 g, 67%.

Compound A7

Compound A6, (3.5 g, 6.75 mMole) was suspended in a 50% solution of dry tetrahydrofuran and diethyl ether. Phosphorus tribromide (0.64 mL, 6.75 mMole) in dry ether (10 mL) was added gradually. After the addition the mixture was gently heated while stirring continued, whereupon a clear solution resulted. This solution was then let stand at room temperature for approximately 15 minutes. At the end of this period the reaction solution was diluted with ethyl acetate, washed with 2N—HCl (x3), dried (MgSO$_4$), filtered and concentrated to an oil. This oil was used as such in the next step of the reaction.

Compound A8

Compound A7 as described above, (6.75 mMole), was dissolved in dimethylformamide (30 mL), and sodium phenylmercaptotetrazole (1.35 g, 6.75 mMole), added. The reaction solution was stirred at room temperature for approximately 15 minutes, diluted with ethyl acetate and the ethyl acetate solution washed with 2N—HCl (x3), dried (MgSO$_4$), filtered and concentrated to an oil. This oil was then pressure chromatographed over silica gel eluting with a solvent mixture of ethyl acetate/dichlormethane/acetic acid in the ratio 15:35:0.5 then 20:30:0.5 to elute the impurities and finally with a ratio of 25:25:0.5 to obtain the product, compound A8.

Yield: 3.0 g, 66% from compound A6. Calculated for $C_{36}H_{42}N_{10}O_2S_1$: %C63.69, %H6.24, %N20.63 and %S4.72. Found: %C63.68, %H6.36, %N20.27 and %S5.32

Synethesis Example B

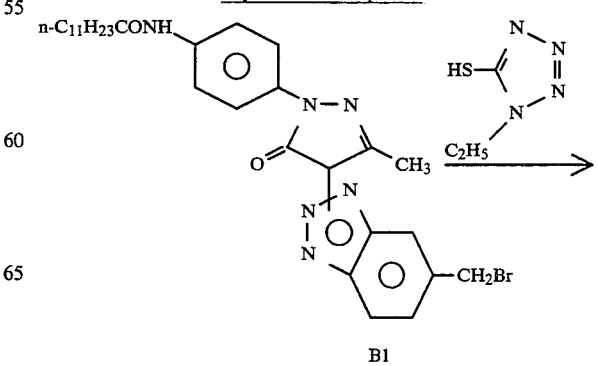

B1

Synethesis Example B

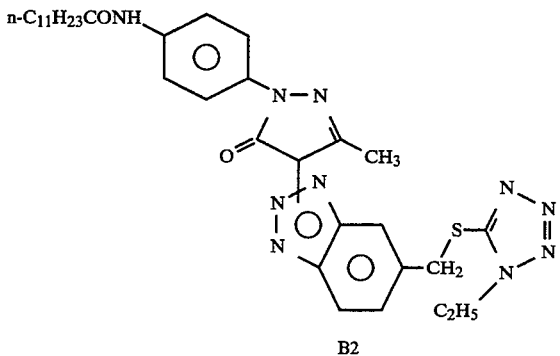

B2

Compound B2

Compound B1, preparation as described in compound A7, (6.75 mMole) was dissolved in dimethylformamide (30 mL), and the cyclohexylamine salt of ethylmercaptotetrazole (1.85 g, 8.1 mMole), added. The reaction solution was stirred at room temperature for approximately 60 minutes, diluted with ethyl acetate and the ethyl acetate solution washed with 2N—HCl (x3), 2.5%-Na$_2$CO$_3$ (x3), 2N—HCl (x1), dried (MgSO$_4$), filtered and concentrated to an oil. This oil was then pressure chromatographed over silica gel eluting with a solvent mixture of ethyl acetate/dichlormethane/methanol/acetic acid in the ratio 15:balance:1:0.1 to obtain the product, compound B2.

Yield: 1.2 g, 28% from compound A6. Calculated for C$_{32}$H$_{42}$N$_{10}$O$_2$S$_1$: %C60.93, %H6.71, %N22.20 and %S5.08. Found: %C60.77, %H6.82, %N21.65 and %S5.88

Synethesis Example C

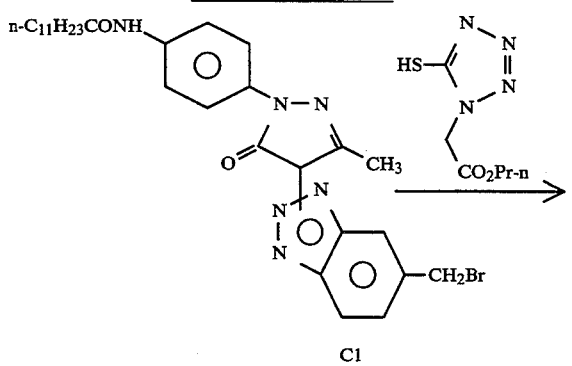

Compound C2

Compound C1, preparation as described in compound A7, (6.75 mMole) was dissolved in dimethylformamide (30 mL), and 1H-tetrazole-1-acetic acid, 2,5-dihydro-5-thioxo-, propyl ester (2.03 g, 6.75 mMole), added. The reaction solution was stirred at room temperature for approximately 60 minutes, diluted with ethyl acetate and the ethyl acetate solution washed with 2N—HCl (x3), 2.5%-Na$_2$CO$_3$ (x3), 2N—HCl (x1), dried (MgSO$_4$), filtered and concentrated to an oil. This oil was then pressure chromatographed over silica gel eluting with a solvent mixture of ethyl acetate/dichlormethane/methanol/acetic acid in the ratio 15:balance:1:0.1 to obtain the product, compound C2.

Yield: 3.0 g, 63% from compound A6. Calculated for C$_{35}$H$_{46}$N$_{10}$O$_4$S$_1$: %C59.81, %H6.60, %N19.93 and %S4.56 Found: %C59.71, %H6.58, %N19.31 and %S4.70 S

Synethesis Example D

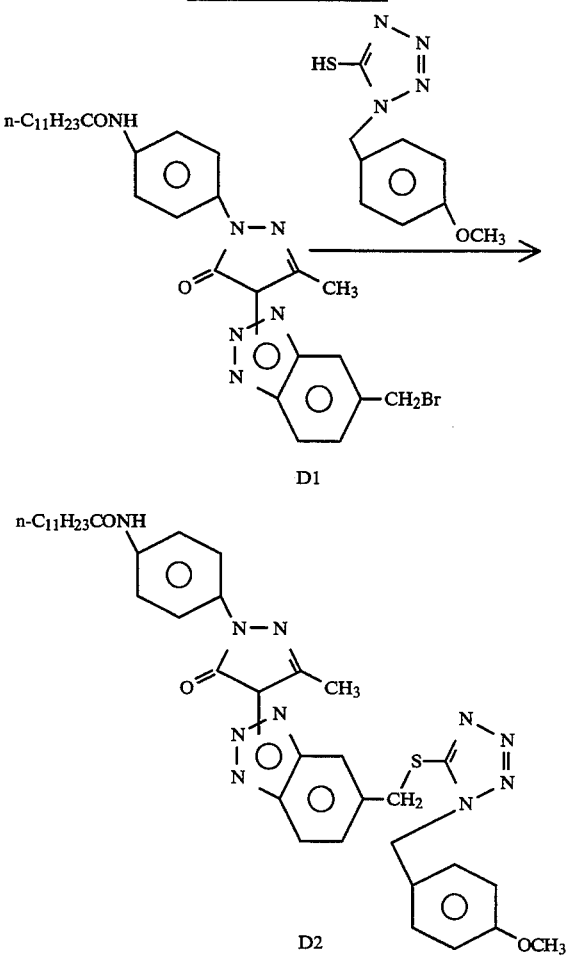

Compound D2

Compound D1, preparation as described in compound A7, (6.75 mMole) was dissolved in dimethylformamide (30 mL), and p-methoxybenzylmercapto-tetrazole (1.5 g, 6.75 mMole), added. The reaction solution was stirred at room temperature for approximately 60 minutes, diluted with ethyl acetate and the ethyl acetate solution washed with 2N—HCl (x3), 2.5%-Na$_2$CO$_3$ (x3), 2N—HCl (x1), dried (MgSO$_4$), filtered and concentrated to an oil. This oil was then pressure chromatographed over silica gel eluting with a solvent mixture of ethyl acetate/dichlormethane/methanol/acetic acid in the ratio 15:balance:1:0.1 to obtain the product, compound C2.

Yield: 2.3 g, 47% from compound A6. Calculated for $C_{38}H_{46}N_{10}O_3S_1$: %C63.14, %H6.41, %N19.38 and %S4.44 Found: %C62.47, %H6.40, %N18.89 and %S5.23

The following examples further illustrate the invention.

EXAMPLES I-1-I-4

Photographic elements were prepared by coating the following layers on a cellulose ester film support (amounts of each component are indicated in mg/m2):

Emulsion layer 1: Gelatin-2420; red sensitized silver bromoiodide (as Ag)-1615; yellow image coupler dispersed in dibuty phthalate (RECEIVER LAYER)

Interlayer: Gelatin-860; didodecylhydroquinone-113

Emulsion layer 2: Gelatin-2690; green sensitized silver bromoiodide (as Ag)-1615; magenta image coupler dispersed in tritolyl phosphate; DIR compound of Table 1 dispersed in N,N-diethyl-dodecanamide and coated at a level sufficient to provide a contrast of 0.5 (half) of the original ontrast after stepwise green light exposure and processing (CAUSER LAYER)

Protective Gelatin-5380;

Overcoat bisvinylsulfonylmethyl ether at 2% total gelatin.

Structures of the image couplers are as follows:

Magenta Image Coupler:

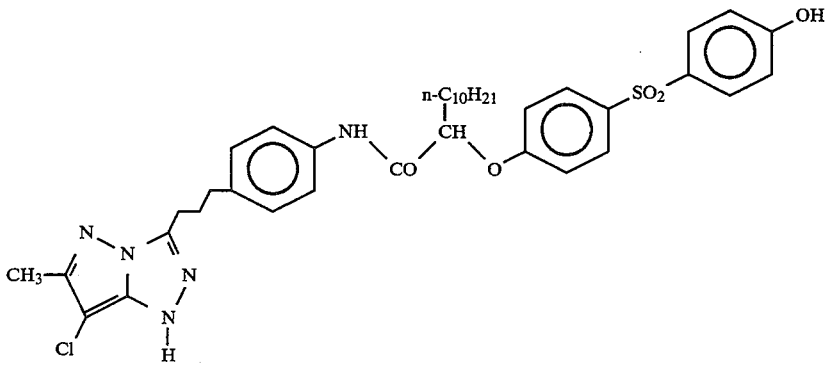

Yellow Image Coupler:

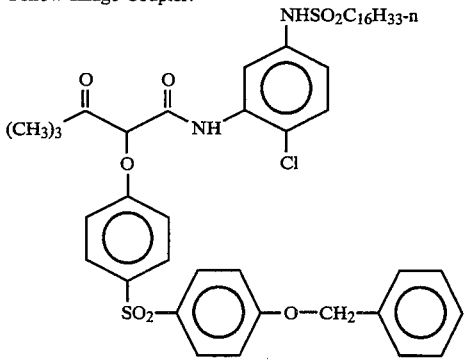

Strips of each element were exposed to green light through a graduated density step tablet, or through a 35% modulation fringe chart for sharpness measurements, and then developed 3.25 minutes at 38° C. in the following color developer, stopped, washed, bleached, fixed, washed and dried.

| Color Developer: | |
|---|---|
| Distilled water | 800 mL |
| Sodium Metabisulfite | 2.78 g |
| Sodium Sulfite, anhydrous | 0.38 g |
| CD-4 (color developer)* | 4.52 g |
| Postassium Carbonate, anhyd. | 34.3 g |
| Postassium Bicarbonate | 2.32 g |
| Sodium Bromide | 1.31 g |
| Potassium Iodide | 1.20 mg |
| Hydroxylamine Sulfate (HAS) | 2.41 g |
| Diethylenetriaminepentacetic acid, pentasodium salt (40% Soln.) | 8.43 g |
| Distilled water Adjust pH to 10.0. | to 1 L |

*CD-4 is 4-amino-3-methyl-N-ethyl-N-beta-hydroxyethylaniline sulfate.

Processed images were read with green light to determine the contrast and AMT acutance. From plots of AMT acutance vs. the logarithm of the contrast for variations in the coated level of each development inhibitor releasing (DIR) compound, the acutance was determined at a contrast of 0.5 compared to its original contrast without the presence of the DIR compound. The acutance for a control DIR coupler was subtracted from each AMT value to provide the relative sharpness value reported as the change in AMT in Table I. AMT calculations employed the following formula in which the cascaded area under the system modulation curve is shown in equation (21.104) on page 629 of the "Theory of the Photographic Process", 4th Edition, 1977, edited by T. H. James: AMT=100+66Log[cascaded area/2.6696M] wherein the magnification factor M is 3.8 for the 35 mm system AMT. The use of CMT acutance is described by R. G. Gendron in "An Improved Objective Method of Rating Picture Sharpness: CMT acutance" in the Journal of SMPTE, Vol. 82, pages 1009–12, (1973). AMT is a further modification of CMT useful for evaluating systems which include the viewing of a positive print made from a negative.

Interimage effect (the degree of color correction) was evaluated after a daylight exposure. Interimage, in this case, was quantified as the ratio of the gamma of the green-sensitive layer (causer) to that of the red-sensitive layer (receiver), ($g_c/g_r$).

TABLE 1

| Coupler No. | Amount to Reduce Gamma Causer ($\gamma_c$) 50% mmoles/ft$^2$ | Interlayer Interimage ($\gamma_c/\gamma_r$) | Acutance Change ΔAMT (35 mm/causer) |
| --- | --- | --- | --- |
| Control-1 | 5 | 1.6 | 0 |
| Comparison-1 | 17 | 1.6 | 0 |
| Comparison-2 | 20 | 2.2 | 2.9 |
| Comparison-3 | ** | — | — |
| I-1 | 9 | 2.1 | 1.0 |
| I-2 | 17 | 2.1 | 2.2 |
| I-3 | 10 | 2.0 | 1.1 |

**Unable to reduce Gamma Causer 50%

TABLE 2

| Coupler No. | Amount to Reduce Gamma Causer ($\gamma_c$) 50% mmoles/ft$^2$ | Interlayer Interimage ($\gamma_c/\gamma_r$) | Acutance Change ΔAMT (35 mm/causer) |
| --- | --- | --- | --- |
| Control-1 | 5 | 1.6 | 0 |
| I-4 | 42 | 2.4 | 2.2 |

Coupler: Control-1

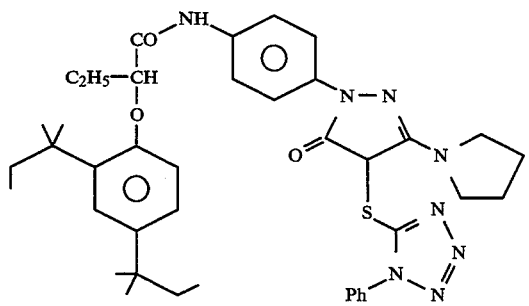

Coupler: Comparison-1

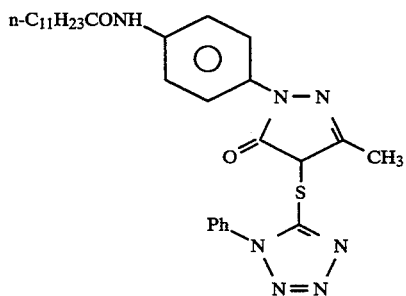

Coupler: Comparison-2

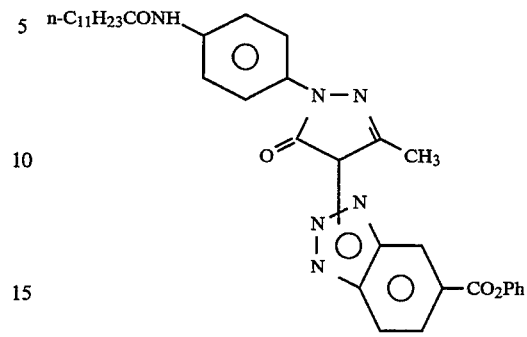

Coupler: Comparison-3

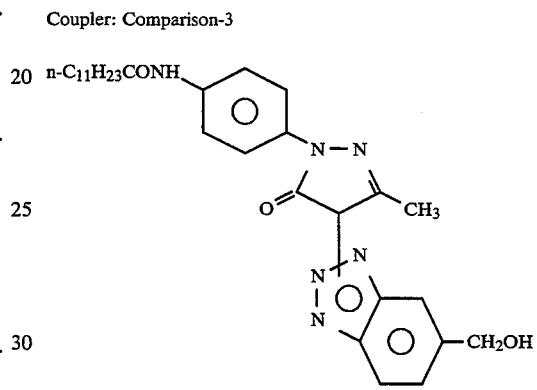

Invention Coupler I-1

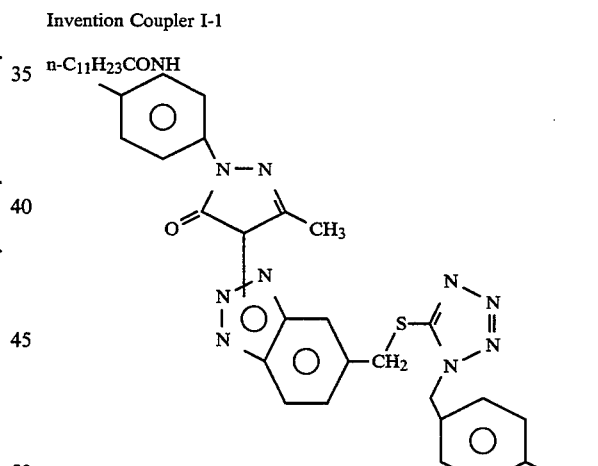

Invention Coupler I-2

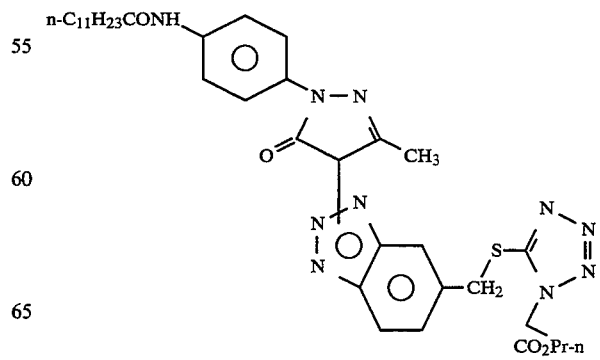

Invention Coupler I-3

TABLE 2-continued

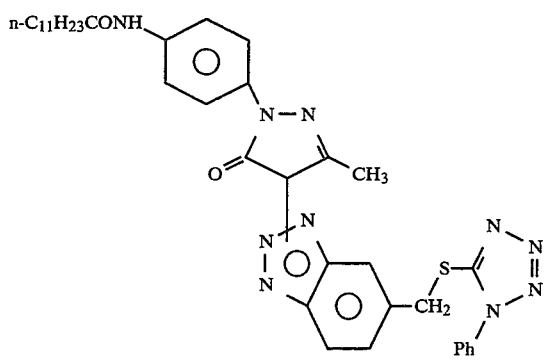

Invention Coupler I-4

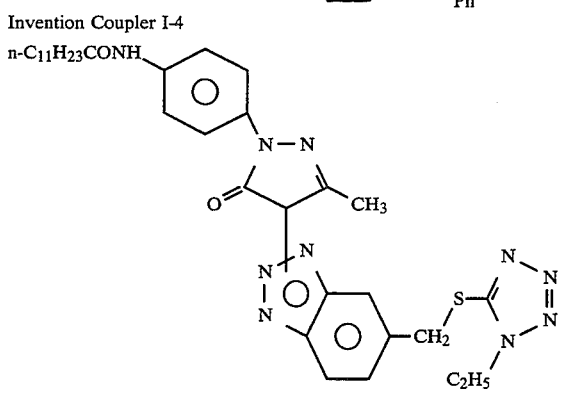

It can be seen from the interimage effects and ΔAMT values in Table I that the use in photographic silver halide elements of couplers of the invention, I-1–I-3, which contain the described combination of groups, leads to improved sharpness, interlayer interimage, and activity-amount needed to reduce the Causer Gamma a specific amount-compared to closely related compounds that do not contain such a combination of groups. Table 2 shows that even with a compound of the invention, I-4, in which Q in the BTAZ-Q group is a weak inhibitor, there is still an increase in interlayer interimage and acutance over the control.

The invention has been described in detail with particular reference to preferred embodiments thereof, but it will be understood that variations and modifications can be effected within the spirit and scope of the invention.

What is claimed is:

1. A method of preparing a 1-aryl-3-substituted-4-heterocyclic-5-pyrazolone development inhibitor releasing coupler having the structure

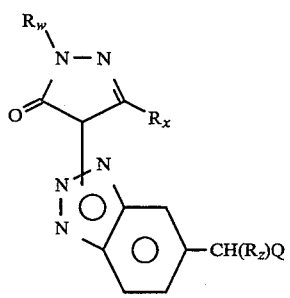

wherein $R_x$ and $R_z$ are independently hydrogen, substituted or unsubstituted alkyl or aryl;

$R_w$ is substituted or unsubstituted alkyl or aryl; at least one of $R_w$ or $R_x$ is a photographic ballast; and Q is a development inhibitor group; comprising:

(a) reacting a haloacyl ester of the formula

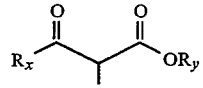

or a haloacylanilide of the formula

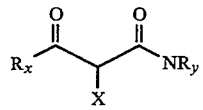

wherein $R_x$ is as defined above;

$R_y$ is hydrogen, substituted or unsubstituted alkyl or aryl; and

X is a halogen with a compound of the formula

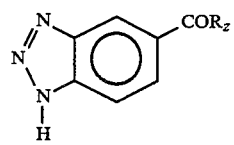

wherein $R_z$ is as defined above;

in the presence of a base to form a first product of the formula

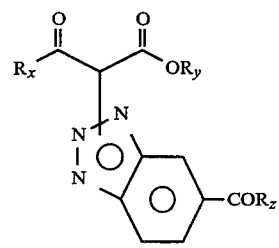

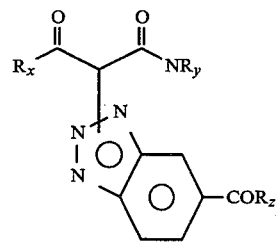

wherein

Rx, Ry and Rz are as defined above;

(b) reacting the first product with a hydrazine compound of the formula

wherein $R_w$ is as defined above; to form a ballasted pyrazolone compound of the formula

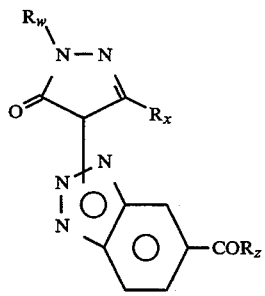

wherein $R_w$, $R_x$, and $R_z$ are as defined above;

(c) reducing the ballasted pyrazalone compound form a compound of the formula

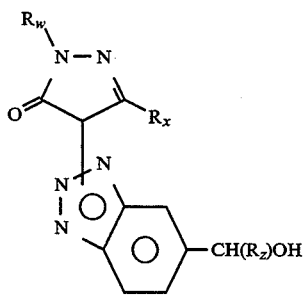

wherein $R_x$, $R_w$ and $R_z$ are as defined above;

(d) halogenating this compound (S7) to form a compound of the formula:

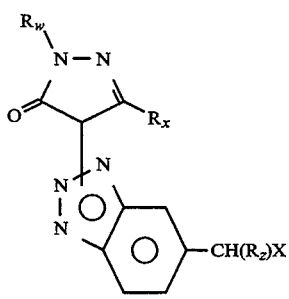

wherein $R_x$, $R_w$, $R_z$ and x are defined above; and then (e) reacting (S8) with a compound having a development inhibitor group Q to form said 1-aryl-3-substituted-4-heterocyclic-5-pyrazolone development inhibitor releasing coupler (S9).

2. The method of claim 1 wherein said pyrazalone development inhibitor releasing coupler prepared is a compound selected from:

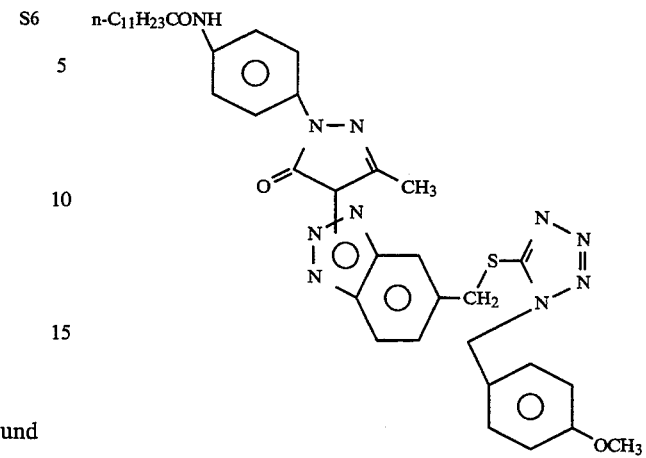

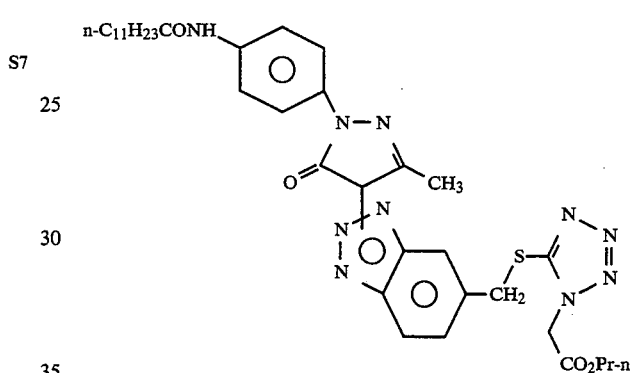

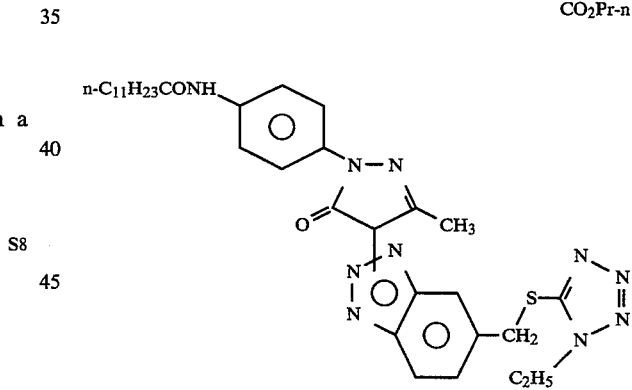

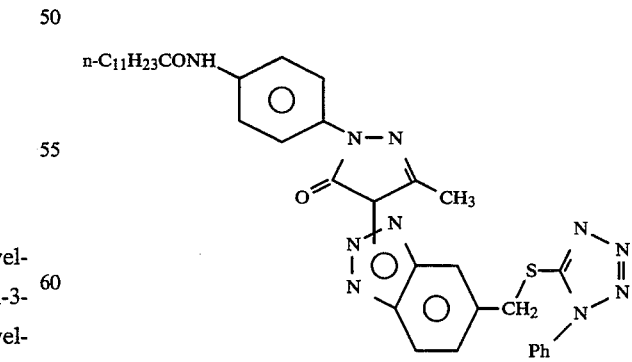

3. A method of preparing a 1-aryl-3-substituted-4-heterocyclic-5-pyrazolone development inhibitor releasing coupler having the structure

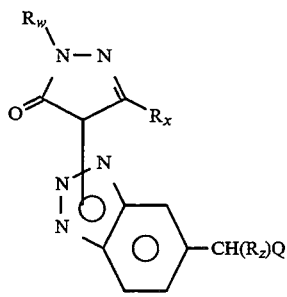

wherein
$R_x$ and $R_z$ are independently hydrogen, substituted or unsubstituted alkyl or aryl;
$R_w$ is substituted or unsubstituted alkyl or aryl; at least one of $R_w$ or $R_x$ is a photographic ballast; and
Q is a development inhibitor group selected from

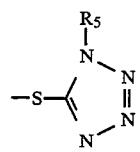

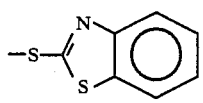

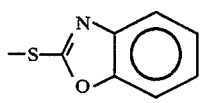

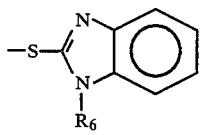

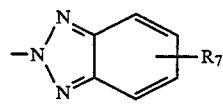

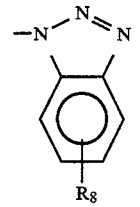

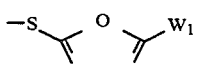

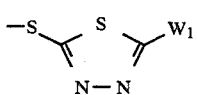

wherein
$R_5$ and $R_6$ are individually hydrogen or alkyls of 1 to 8 carbon atoms;

$R_7$ and $R_8$ are individually selected from the group consisting of hydrogen, halogen, alkyl of 1 to 4 carbon atoms, carboxyl, ester, —NHCOOCH$_3$, —SO$_2$OCH$_3$, —OCH$_2$CH$_2$SO$_2$CH$_3$, —OC(O)OCH$_2$CH$_3$, —NHC(O)C(O)OCH$_3$ and NO$_2$; and
$W_1$ is an unsubstituted or substituted alkyl or aryl;
comprising:
(a) reacting a haloacyl ester of the formula

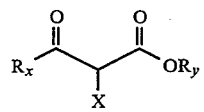

or a haloacylanilide of the formula

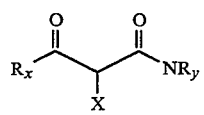

wherein
$R_x$ is as defined above;
$R_y$ is hydrogen, substituted or unsubstituted alkyl or aryl; and
X is a halogen with a compound of the formula

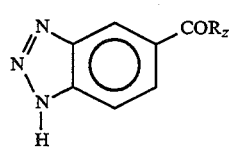

wherein
$R_z$ is as defined above; in the presence of a base to form a first product of the formula

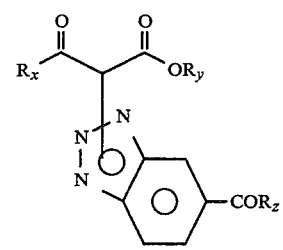

or

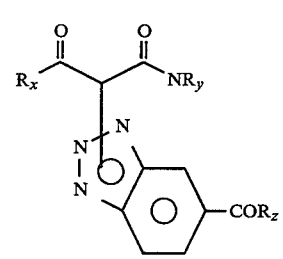

wherein
Rx, Ry and Rz are as defined above;
(b) reacting the first product with a hydrazine compound of the formula $R_wNHNH_2$      S5 wherein
R$_w$ is as defined above; to form a ballasted pyrazolone compound of the formula

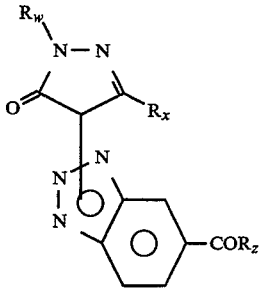
S6 wherein
R$_w$, R$_x$, and R$_z$ are as defined above;

(c) reducing the ballasted pyrazalone compound form a compound of the formula

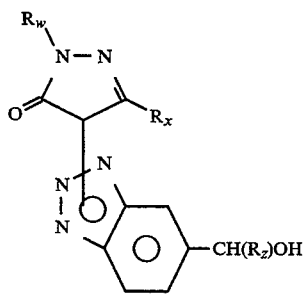
S7 wherein
R$_x$, R$_w$ and R$_z$ are as defined above;

(d) halogenating this compound (S7) to form a compound of the formula:

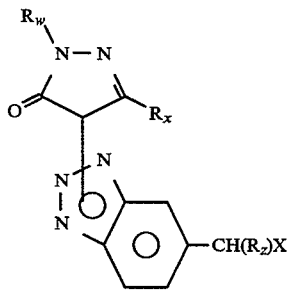
S8 wherein
R$_x$, R$_w$, R$_z$ and x are defined above; and then (e) reacting (S8) with a compound having a development inhibitor group Q to form said 1-aryl-3-substituted-4-heterocyclic-5-pyrazolone development inhibitor releasing coupler (S9).

4. A method of preparing a 1-aryl-3-substituted- 4-heterocyclic-5-pyrazolone development inhibitor releasing coupler having the structure

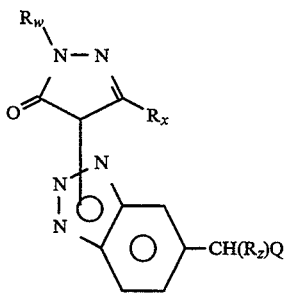
S9 wherein
R$_x$ and R$_z$ are independently hydrogen, substituted or unsubstituted alkyl or aryl;
R$_w$ is substituted or unsubstituted alkyl or aryl; at least one of R$_w$ or R$_x$ is a photographic ballast; and
Q is a development inhibitor group selected from

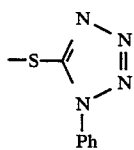

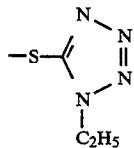

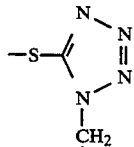

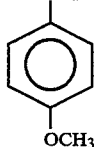

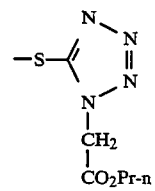

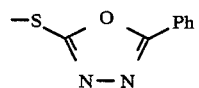

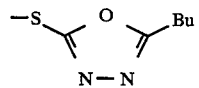

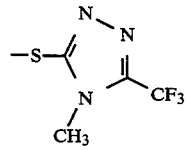

-continued

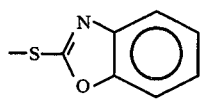

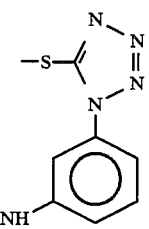

comprising:
(a) reacting a haloacyl ester of the formula

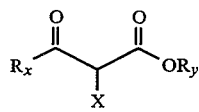
S2A or a haloacylanilide of the formula

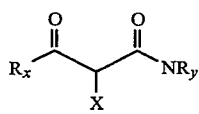
S2B wherein
$R_x$ is as defined above;
$R_y$ is hydrogen, substituted or unsubstituted alkyl or aryl; and
X is a halogen with a compound of the formula

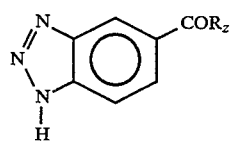
S3 wherein
$R_z$ is as defined above; in the presence of a base to form a first product of the formula

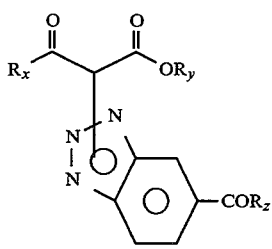
S4A or

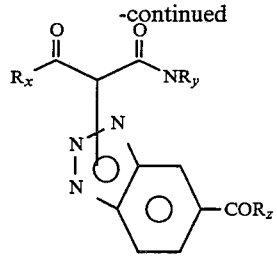
S4B wherein
$R_x$, $R_y$ and $R_z$ are as defined above:
(b) reacting the first product with a hydrazine compound of the formula $R_wNHNH_2$  S5 wherein
$R_w$ is as defined above; to form a ballasted pyrazolone compound of the formula

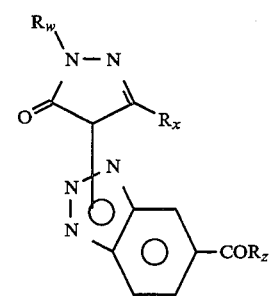
S6 wherein
$R_w$, $R_x$, and $R_z$ are as defined above;
(c) reducing the ballasted pyrazalone compound to form a compound of the formula

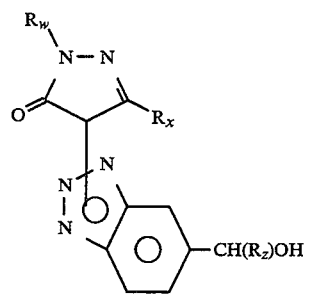
S7 wherein
$R_x$, $R_w$ and $R_z$ are as defined above;
(d) halogenating this compound (S7) to form a compound of the formula:

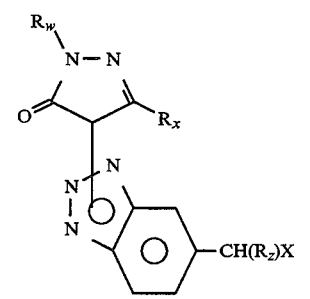
S8 wherein
$R_x$, $R_w$, $R_z$ and x are defined above; and then
(e) reacting (S8) with a compound having a development inhibitor group Q to form said 1-aryl-3-substituted-4-heterocyclic-5-pyrazolone development inhibitor releasing coupler (S9).

* * * * *